(12) United States Patent
Sakai et al.

(10) Patent No.: US 8,216,776 B2
(45) Date of Patent: Jul. 10, 2012

(54) DIALYSATE OF PERITONEAL DIALYSIS AND ITS PREPARATION METHOD

(75) Inventors: Asahi Sakai, Sakura (JP); Masaaki Nakayama, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 12/662,907

(22) Filed: May 11, 2010

(65) Prior Publication Data

US 2010/0221147 A1  Sep. 2, 2010

Related U.S. Application Data

(62) Division of application No. 11/704,931, filed on Feb. 12, 2007, now abandoned, which is a division of application No. 10/380,350, filed as application No. PCT/JP01/07772 on Sep. 7, 2001, now abandoned.

(30) Foreign Application Priority Data

Sep. 13, 2000  (JP) ................. 2000-277810
Feb. 16, 2001  (JP) ................. 2001-040718
Jun. 20, 2001  (JP) ................. 2001-186642

(51) Int. Cl.
*A01N 1/00* (2006.01)
(52) U.S. Cl. ........................ 435/1.2; 424/711
(58) Field of Classification Search .......... None
See application file for complete search history.

(56) References Cited

U.S. PATENT DOCUMENTS

| 3,617,451 | A | * | 11/1971 | Slominski et al. ............ 205/217 |
| 4,100,098 | A | * | 7/1978 | Magan ..................... 252/186.25 |
| 4,929,378 | A | | 5/1990 | Morita et al. |
| 5,610,170 | A | | 3/1997 | Inoue et al. |
| 6,248,726 | B1 | | 6/2001 | Alsop et al. |
| 6,252,054 | B1 | | 6/2001 | Ogino et al. |

FOREIGN PATENT DOCUMENTS

| DE | 3620845 | 12/1987 |
| EP | 0928615 | 7/1999 |
| JP | 5-58604 | 8/1993 |
| JP | 7-136255 | 5/1995 |
| JP | 8-337590 | 12/1996 |
| WO | 00/10606 | 3/2000 |
| WO | 00/20052 | 4/2000 |
| WO | 01 89478 | 11/2001 |
| WO | 02 053094 | 7/2002 |

OTHER PUBLICATIONS

Goodhead K. et al. The Non-oxidative Decomposition of Heated Sodium Dithionite, J. appl. Chem. Biotechnol. 1974, 24: 71-79.*
Oren A. et al. *Ectothiorhodospira marismortui* sp. nov., an obligately anaerobic, moderately halophilic purple sulfur bacterium from a hypersaline sulfur spring on the shore of the Dead Sea, Arch Microbiol (1989) 151:524-529.*
Mohn et al. Catabolic Thiosulfate Disproportionation and Carbon Dioxide Reduction in Strain DCB-1, a Reductively Dechlorinating Anaerobe, Journal of Bacteriology, Apr. 1990, 172(4): 2065-2070.*
Halaby, S. F. et al., entitled "Absorption of Sodium Bisulfite From Peritoneal Dialysis Solutions", Journal of Pharmaceutical Association, Washington, US, vol. 54, No. 1, Jan. 1965, pp. 52-55, (XP002946328).
Lang, K., et al., entitled "Sulfit in Infusionsloesungen", Zeitschrift Fuer Ernaehrungswissenschaft, Steinkopf Verlag, Darmstadt, DE, vol. 18, No. 1, 1979, pp. 37-41, (XP002946330).
Howell, S. B., et al., entitled "Intraperitoneal CIS-Diamminidichloroplatium With Systemic Thiosulfate Protection", Cancer Research, American Association for Cancer Research, Baltimore, MD, US, vol. 43, Mar. 1983, pp. 1426-1431, (XP002946327).
Wieslander, A. P., et al., entitled "Heat Sterilization of Glucose-Containing Fluids for Peritoneal Dialysis: Biological Consequences of Chemical Alterations", Peritoneal Dialysis International, Pergamon Press, New York, NY, US, vol. 15, No. 7, Suppl. 1995, pp. S52-S60, (XP002946331).
Fuminori, Kato, et al., "Immunosuppressive Effects of 3, 4-Dideoxyglucsone-3-ene, An Intermediate in the Maillard Reaction", Journal of Agricultural and Food Chemistry, American Chemical Society, Washington, US, vol. 42, No. 9, 1994, pp. 2068-2073, (XP002966230).
Torbjorn, Linden, et al., entitled "3-Deoxyglucosone, A Promoter of Advanced Glycation End Products in Fluids for Peritoneal Dialysis", Peritoneal Dialysis International, Pergamon Press, New York, NY, US, vol. 18, No. 3, May 1992, pp. 290-293, (XP002966246).
The Term "Electrolyte" Merriam-Webster Online Dictionary. See at http://www.m-w.com. p. 1, Accessed on Nov. 23, 2005.
Millo A. et al. Changes in the permeability of the isolated frog heart irradiated with X-rays. Protective action of glucose, of cysteamine, and of sodium thiosulfate. Rivista di Biologia, 1964, 2:151-167, 169-181, entire document.
Grant & Hackh's Chemical Dictionary, Fifth edition, 1987, pp. 542-543, and 559.
Twardowski Z.J. et al, Osmotic agents and ultrafiltration in preitoneal dialysis, Nephron, 1986, 42(2):93-101. A review, entire document.

* cited by examiner

*Primary Examiner* — Jon P Weber
*Assistant Examiner* — Satyendra Singh
(74) *Attorney, Agent, or Firm* — Wenderoth, Lind & Ponack, L.L.P.

(57) ABSTRACT

An aqueous solution of electrolytes, a sugar osmotic agent and a physiologically safe salt of a reductive sulfur oxy-acid. Alternatively, the dialysate comprises an aqueous solution of electrolytes, a salt of a reductive sulfur oxy-acid, and osmotic agents which contain an oncotic agent other than a sugar osmotic agent.

1 Claim, No Drawings

DIALYSATE OF PERITONEAL DIALYSIS AND ITS PREPARATION METHOD

This application is a divisional of Ser. No. 11/704,931, filed Feb. 12, 2007, now abandoned which is a divisional of Ser. No. 10/380,350, filed Mar. 13, 2003, now abandoned; which was a 371 U.S. national stage of International Application No. PCT/JP01/07772, filed Sep. 7, 2001, herein incorporated by reference in their entirety.

FIELD OF THE INVENTION

The present invention relates to the dialysate for peritoneal dialysis, that is, therapy for end stage renal disease, more specifically, the dialysate for peritoneal dialysis to suppress protein cross linking due to sugar osmotic agents, such as glucose and the like.

BACKGROUND OF THE INVENTION

The peritoneal dialysis has been applied as an effective therapy for end stage renal disease patients. The dialysis is proceeded by infusing dialysate into peritoneal cavity through a catheter, which is implanted in the patient's peritoneal cavity, and storing it for a certain period, thence withdrawing the dialysate out through the catheter. This procedure is repeated a few times every day.

This dialysis has a few advantages over hemodialysis in physiological point of view, as it purifies blood continuously through the patients' peritoneum, while hemodialysis purifies blood though an artificial membrane intermittently. Also peritoneal dialysis enables the patients' social activity, so that the peritoneal dialysis has been widely applied.

In hemodialysis, removal of excess liquid is achieved by raising the pressure of blood line over that of the dialysate line. However the same means can not be applied to peritoneal dialysis, therefore an osmotic agent is added into the dialysate so as to raise the osmotic pressure of the dialysate over that of plasma. The dialysate is infused into the peritoneal cavity to contact to peritoneum for removing excess liquid from the patient's body. For this purpose, glucose has been used as an osmotic agent. Glucose had been recognized to be safe and physiological, and to cause no problem on metabolism after it is absorbed into the body.

However, adverse effects were recognized as serious problems, such as disfunctioning of peritoneum, due to the absorption of large quantity of glucose into the patient body and the reaction with amino acids, peptide and protein, followed by the formation of AGEs, progress of collagen synthesis, and cross linking of protein. Consequently it causes peritoneum sclerosis and leads to cease of the therapy.

The cross linking reaction of protein molecules with glucose is assumed to take place as follows;

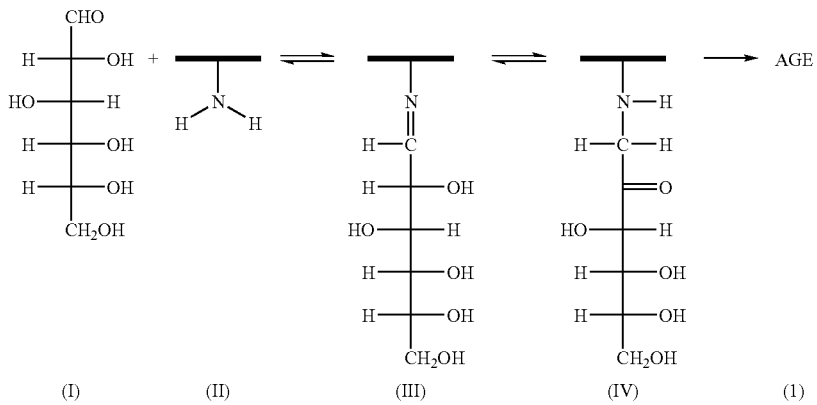

Carbonyl residue(s) containing sugars, such as glucose and the like, react with amino acids, peptides or protein (II), and through Shiff base (III) and Amadori compounds (IV), lead to advanced glycation end products (AGE); the cross linking between protein molecules Also it has been reported that glucose is converted through dialysate sterilization process under high pressure and temperature to the following compounds, that is called glucose degradation products (GDP);
glyoxal,
methylglyoxal
3-deoxyglucosone.

The above-described GDPs are more reactive substances for AGE formation compared to sugars per se. When dialysate contains the GDPs, the protein cross linking reaction is accelerated by a few dozen to a few thousands times as fast as when the dialysate contains glucose alone.

An example of protein cross linkage formed in AGEs by the reaction between carbonyl residues of sugar or GDP and amino residues of lysine or arginine that constitutes protein molecules is shown as formula (2).

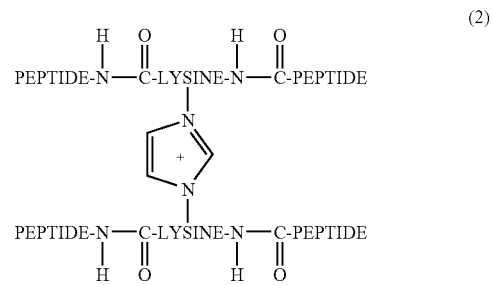

As one of the means for the solution of this problem, the modification of heat sterilization conditions for the dialysate has been proposed, but it can not prohibit the protein cross linking completely, and cross-linking reaction of protein by glucose itself may not be disregarded. So that effective prohibition means of protein cross linking are required for peritoneal dialysis.

The inventors of the present invention has proposed the technology wherein the patient's plasma protein, which is migrated out to dialysate, is recovered from peritoneal dialysis effluent and after the concentration, it is used as an osmotic agent for substituting a part or all of glucose. (Japanese Patent Application Hei 8-150930 and Hei 9-302388). However as long as glucose is used as a portion of osmotic agents, the problem of protein cross linking may not be solved completely.

DESCRIPTION OF THE INVENTION

The inventors of the present invention understood protein cross linking with glucose or GDPs takes place through the afore-described mechanism and assumed that the protein cross linking reaction may be suppressed by addition of the inhibitors of the reaction, and searched a variety of chemical compounds which they assumed to be inhibitors. Resultantly, they found a number of effective compounds in suppression of the protein cross linking.

Also they found effective compounds that may split cross linkage of protein, even after cross linkage is formed Briefly the present invention relates to the dialysate of peritoneal dialysis which comprises aqueous solution of electrolyte, sugars as osmotic agents and the inhibitors of protein cross linking and/or the splitters of protein cross linkage as additives And also the present invention relates to the preparing method of the dialysate of peritoneal dialysis containing the protein cross linking inhibitors and/or the splitters of protein cross linkage, and their sterilizing method without decomposition of the inhibitors of protein cross linking.

MOST PREFERABLE EMBODIMENT FOR CARRYING OUT THE INVENTION

In the present invention, sugars are used as osmotic agents for the dialysate of peritoneal dialysis. The example of the sugars are monosaccharides such as glucose, mannose, and the like, disaccharides such as sucrose, fructose and the like, or oligomer and polymers such as dextran, dextrin and the like. Also the dialysate may contain amino acids, peptides and protein in addition to sugars.

The electrolytes may be mixture of sodium chloride, magnesium chlorides, calcium chloride, sodium lactate, sodium bicarbonate and the like. The composition and the concentration of the electrolytes are favorably close to those of the serum. When the concentration of calcium and magnesium in the patients serum differs from the ordinal value due to drug dosage for complication, the adjusted dialysate in calcium and magnesium concentration are preferably used.

In the present invention, the inhibitors of protein cross linking, as additives to the aqueous solution of electrolytes and sugars, may be used if they are physiologically safe and inhibit AGE reaction at any stage.

Also the splitters of protein cross linkage may be used if they split protein cross linkage under physiological conditions and their reaction products are not toxic.

Generally speaking, reductants may be effective suppresser of cross linking

The reductants having lower redox potential may be more effective suppresser. Especially those having lower redox potential compared to that of saline solution (+160 mV~+180 mV) are effective.

More specifically, examples of effective suppressers of cross linking, which fall into reductants, anti-oxidants or other compounds than the above described, may be mercaptan, sulfides, hydrosulfides, salts of reductive sulfur oxy-acid, thiourea and their derivatives, hydroxyl or carboxyl residue(s) containing, cyclic compounds, flavonoids, nitrogen containing hetero cyclic compounds, hydrazil compounds, uronic acid(s) containing mucopolysaccharides. While examples of splitters of protein cross linkage may be thiazole derivatives Examples of mercaptan, i.e. those having mercapto (—SH) residue(s), may be cysteine, acetylcysteine, mercaptoethanol, glutathione, dithioerythrytol, N-acetylmercaptosuccinic anhydride and the like.

Examples of sulfides and hydrosulfides may be sodium sulfide, sodium hydrosulfide and the like.

Examples of salts of reductive sulfur oxy-acid may be sodium, potassium, or other physiologically safe salts of sulfite, bisulfite, thio-sulfate, metabisulfite (disulfite) or dithionite. These salts may be acidic salts (for example acid bisulfite) as well as neutral salts Examples of thiourea and its derivatives are thiourea, dimethyl thiourea and the like.

Examples of hydroxyl and/or carboxyl residue(s) containing cyclic compounds may be acetyl salicylic acid, ascorbic acid, or their sodium salts or other physiologically safe salts.

Examples of flavonoids may be hetero-cyclic compounds which contain more than two hydroxyl residues, such as quercetin dihydrate, catechin, epicatechin, or their hydrates, Examples of nitrogen containing hetero cyclic compounds may be thiazole, thiazoline, thiazolidine, triazole, tetrazole, indole, imidazole, pyridine, and pyrimidine cycles.

Examples of thiazole containing cyclic compounds may be N-(2-thiazolyl) sulfanilamide, N-phenacyl thiazolium bromide. The latter compound may reacts with the cross linked protein to split the linkage.

Example of indole containing cyclic compounds may be N-acetyltriptophan.

Example of triazol containing cyclic compounds may be 4-(1, 2, 3, 4-thiatriazo-5-rylamino) phenol Example of thiazoline containing cyclic compounds which comprise may be 2-mercaptothiazoline.

Example of thiazolidine containing cyclic compounds may be 2-Oxothiazolidine-4-carboxylic acid Example of hydrazil compounds may be aminoguanidine hydrochloride.

Example of uronic acid(s) containing mucopolysaccharides may be heparin

The dose of the protein cross linking suppressors may vary in the range of 0.1~200 weight %, preferably 1~100 weight %. When the dose is too low, the suppression effect of protein cross linking would be insufficient, while the dose is too high, it may cause poor dissolving in dialysate.

The concentration of sugar osmotic agents may be adequate in the range of 5~300 mOsm/l in addition to that of electrolytes. When the concentration of sugar osmotic agents is too low, adequate ultra filtration may not be achieved, while if it is too high, it causes adverse effects such as worsening of diabetes mellitus.

Additionally, oncotic agents other than sugar osmotic agents may be added into dialysate as much as they indicate significant oncotic pressure. Examples of the oncotic agents may be polymers such as albumin, globulin and the like.

These oncotic agents are not restricted to be chemical reagents nor medical intravenous solution, but a mixture of serum protein which is recovered from the patient's own effluent of peritoneal dialysis The recovery method is described in the Japanese Patent Application number Hei 8-150930 and Hei 9-302388 filed by the inventor of the present invention, that is, concentrating the effluent through a semi permeable membrane and diluting the condensate with water or electrolyte solution, followed by repeating these procedures so as to refine the protein, or alternately adding acid into the concentrate, followed by de-acidification by membrane dialysis with water to deposit the protein at the iso-electric point, thence separating the deposit from supernatant and re-dissolving it into fresh dialysate as oncotic agent, The dialysate may be supplemented by additional oncotic agents too.

By substituting a part of sugar osmotic agents with non-sugar oncotic agents, dose of the sugar can be decreased, so that protein cross linking due to sugar can be suppressed. In the dialysate containing oncotic agents, the concentration of oncotic agents may be preferable in the range of 0.1~30 g/dl.

The dialysate of peritoneal dialysis in the present invention is prepared by addition of protein cross linking suppressor(s) and/or protein cross linkage splitter(s) into the solution of electrolytes and sugar osmotic agent. Conventional dialysate is sterilized by heating at 110° C. or higher temperature. Also pH of the dialysate is lowered down to around 5.0-5.8.

When the cross linking suppressor(s) are added and the dialysate is heat sterilized, some instable suppressor(s) or the splitter(s) are decomposed. In such a case, it is preferable that the dialysate is sterilized separately, thence the suppressor(s) or the splitter(s) are added before use. If heat labile compound(s) are added into the dialysate, it is desirable not to sterilize by heating it but to sterilize it by filtering it through nano-filter(s).

The sugar osmotic agents which is used in the present invention may be glucose and the like that have reductive terminal residue(s), and tends to decompose easily through heat sterilization. In autoclave, if the sugar osmotic agents and heat stable suppressor(s) such as bisulfite, sulfite, sulfide, hydrosulfide and the like are sterilized together, the decomposition reaction of glucose may be suppressed, and consequently the concentration of glucose degradation products could be decreased below a detectable level.

EXAMPLES

The advantages of the present invention are explained by citing the results of actual verification examples. In the verification tests, the degree of protein cross linking by AGE formation were estimated by the determination of fluorescent intensity, based on the phenomenon that AGEs emits fluorescence, (Reference: Lee K. W. et al: "A systematic approach to evaluate the modication of lens protein by glycation-induced cross linking" *Biochim. Biophys Acta:* 1453(1) 141-151 Jan. 6, 1999)
(Estimation of Suppression Effect on Protein Cross Linking by Fluorescent Intensity)

Example 1

For estimating the suppression effect on protein cross linking sensitively, glyoxal was used. This chemical is one of glucose degradation products and much greater promoter to accelerate AGE formation than glucose does. Glyoxal (20 mM/l) was added into phosphate buffer solution, in which human serum albumin (50 mg/ml) was dissolved. As a test specimen, mercapto compound, listed in Table 1, was added into the solution at 20 mM/l, then incubated at 37° C. as long as for two weeks. Fluorescent intensity (FI) of the cross linked albumin in the incubated solution was determined at 440 nm (excitation: at 370 nm) by fluorescence meter (Nihon Bunkou Co.). The suppression effect was estimated as follows; dividing the increase in the fluorescent intensity through the incubation in the case of "test specimen added", by that of "no test specimen added (control 1)". The result is shown in Table 1.

Control 1

In Control test 1, the fluorescent intensity was determined in the same manner as those in Example 1

TABLE 1

| | | Specimen (Cross linking Suppressors) | Increase in FI % |
|---|---|---|---|
| Example 1 | (a) | N-Acetylcysteine | 7 |
| | (b) | 2-Mercaptoethanol | 42 |
| | (c) | Dithio erythrytol | 31 |
| | (d) | Glutathione | 25 |
| | (e) | S-Acetylmercaptosuccinic anhydride | 50 |
| | (f) | Dimethylcysteine (Penicillamine) | 83 |
| | (g) | Thiodiglycol | 91 |
| Control 1 | | Control (no specimen added) | 100 |

Example 2

Methylglyoxal in place of glyoxal as GDP (Glucose Degradation Products) in Example 1 was used under the similar conditions as Example 1. Sodium bisulfite and sodium sulfite were tested as protein cross linking suppressors. Fluorescent intensity was determined in the same manners as in Example 1. The results are shown in Table 2.

Control 2

No protein cross linking suppressor, but methylglyoxal alone was added to human serum albumin. Fluorescent intensity was determined in the same manners as Example 2. The results are shown in Table 2.

TABLE 2

| | | Specimen(Cross linking suppressors) | Increase in FI (%) |
|---|---|---|---|
| Example 2 | (a) | Sodium bisulfite | 46 |
| | (b) | Sodium sulfite | 61 |
| Example 3 | (a) | Acetyl salicylic acid | 53 |
| | (b) | Ascorbic acid | 86 |
| Example 4 | (a) | Quercetin dihydrate | 19 |
| | (b) | Catechin hydrate | 64 |
| | (c) | Epicatechin | 72 |
| Example 5 | | Heparin | 96 |
| Example 6 | | Amino guanidine hydrochloride | 31 |
| Example 7 | | N-Phenacyl thiazolium bromide | 28 |
| Example 8 | (a) | N-(2-thiazolyl)-sulfanylamide | 45 |
| | (b) | 2-mercapto-4-methyl-thiazole acetic acid | 82 |
| | (c) | 4-(1,2,3,4-thia triazo)phenol hydrate | 92 |
| | (d) | 2-Oxo-thiazolidine-4-carboxylic acid | 8 |
| | (e) | 2-Mercaptothiazoline | 48 |
| Control 2 | | Control (No suppressor added) | 100 |

Example 3

The cross linking suppressors in Example 2 were replaced by acetylsalicylic acid and ascorbic acid and other conditions were similar to those in Example 2. The increase in fluorescent intensity was determined to estimate relative ratio to those of Control 2. The results are shown in Table 2.

Example 4

The cross linking suppressors in Example 2 were replaced by quercetin dihydrate, catechin hydrate or epicatechin which were dissolved into dimethylsulfoxide, thence phosphate buffer solution was added at the ratio 1:3. The increase in fluorescent intensity was determined to estimate relative ratio to those of Control 2. The results are shown in Table 2.

Example 5

The cross linking suppressors in Example 2 were replaced by heparin, and other conditions were similar to those in Example 2. The increase in fluorescent intensity was determined to estimate relative ratio to those of Control 2. The results are shown in Table 2.

Example 6

The cross linking suppressors in Example 2 were replaced by amino guanidine, and other conditions were similar to those in Example 2. The increase in fluorescent intensity was determined to estimate relative ratio to those of Control 2. The results are shown in Table 2.

Example 7

The cross linking suppressors in Example 2 were replaced by N-phenacylthiazolium bromide which was dissolved into mixture of methanol and phosphate buffer solution at the ratio of 1:1 at 20 mM/l.

The increase in fluorescent intensity was determined to estimate relative ratio to those of Control 2. The results are shown in Table 2.

Example 8

The cross linking suppressors in Example 7 were replaced by N-(2-thiazolyl)-sulfanilamide, 2-mercapto-4-methyl-thiazole acetic acid, 4-(1, 2, 3, 4-thia triazo) phenol hydrate, 2-Oxo-thiazolidine-4-carboxylic acid, or 2-Mercaptothiazoline.

Each compound was dissolved at the concentration of 20 mM/l respectively in the mixture of dimethylsulfoxide and phosphate buffer solution at the ratio of 1:3. The increase in fluorescent intensity was determined to estimate relative ratio to those of Control 2. The results are shown in Table 2.

Example 9

Control 3

Collagen IV, methylglyoxal and one of the chemicals listed in Table 3 was dissolved into phosphate buffer solution, and incubated at. 37° C. as long as for 7 days. The increase in fluorescent intensity was determined to estimate relative ratio to those of Control 3, wherein methylglyoxal alone was added to collagen IV The test results are shown together with their redox potential in Table 3.

TABLE 3

| Specimen (Cross linking suppressors) | | Increase in FI % | Redox potential (mV) |
|---|---|---|---|
| Example 9 | (a) Sodium sulfide ($Na_2S$) | 19 | −616 |
| | (b) Sodium hydrosulfide (NaHS) | 10 | −620 |

TABLE 3-continued

| Specimen (Cross linking suppressors) | | Increase in FI % | Redox potential (mV) |
|---|---|---|---|
| | (c) Sodium thiosulfate ($Na_2S_2O_3$) | 67 | +40 |
| | (d) Sodium metabisulfite ($Na_2S_2O_5$) | 0 | +17 |
| | (e) Sodium hydrosulfite (dithionite) ($Na_2S_2O_4$) | 0 | −360 |
| | (f) Dimethylthiourea | 2 | −40 |
| | (g) Sodium bisulfite ($NaHSO_3$) | 0 | −127 |
| Control 3 | No suppressor added | 100 | +282 |

The compounds in Table 3 are all known to be reductants having lower redox potential than that of saline solution; +160~+180 mV.

It is apparent that the reductants having lower redox potential than that of saline solution are effective suppressors of protein cross linking.

(Quantitative Analysis of GDPs by Redox Potential Titration)

Example 10

Control 4

The solution of sodium chloride and glucose was heated at 125° C. for 45 minutes in an autoclave and GDP was analyzed by redox potential titration method with 0.1 M/l standard sodium thiosulfate solution. The results are shown in Table 4.

TABLE 4

| | Additives | Additive concentration (µM/l) | GDP concentration (µM/l) |
|---|---|---|---|
| Example 10 | (a) Sodium bisulfite | 100 | Not detected |
| | (b) Sodium hydrosulfide | 50 | Not detected |
| | (c) Lactic acid | 35,000 | 185 |
| | (d) Sodium bicarbonate | 15,000 | 860 |
| Control 4 | No additive | — | 560 |

(Effects of Protein Cross Linkage Splitter)

Example 11

Human serum albumin was dissolved in phosphate buffer solution at 50 mg/ml, wherein 3-deoxyglucosone was added at 50 mM/l, thence the solution was incubated at 37° C. for 7 days, followed by the determination of fluorescent intensity. Residual 3-deoxyglucosone was removed by membrane dialysis with phosphate buffer solution. N-phenacyl thiazolium bromide was added at 20 mM/l concentration into the albumin solution (mixture of ethanol: phosphate buffer solution 1:1), Thence another 7 days incubation was proceeded at 37° C. The fluorescent intensity after the second incubation ($14^{th}$ day) was compared with $7^{th}$ day value. The decrease in FI is shown in Table 5.

Example 12

Epicatechin and catechin dihydrate were dissolved into a mixture of dimethylsulfoxide (DMSO): phosphate buffer solution (1:3) at 20 mM/l in place of N-phenacyl thiazolium bromide in Example 11 and used for the incubation for 7 days in the same manner as in Example 9. After 14 day incubation, the intensity of fluorescence (IF) was determined and the decrease in IF from that of after 7 days incubation was estimated. The results are shown in Table 5.

TABLE 5

|  | Additives added after 7 days | Decrease % |
|---|---|---|
| Example 11 | N-Phenacyl thiazolium bromide | −21% |
| Example12 (a) | Epicatechin | −6% |
| Example12 (b) | Catechin dihydrate | −4% |

It is apparent in Table 5 that the cross linkage in the albumin formed by 3-deoxyglucosone was split by N-phenacyl thiazolium bromide.

(Determination of Suppression Effect on AGE Formation in Peritoneum Tissue)

Control 5

Intra-peritoneal infusion of 15 ml of solution (A) listed in Table 6 was performed into peritoneal cavity of 7 weeks old rats (weight:300±15 g) every day for 5 days, thence the parietal peritoneum tissue was taken, frozen and sliced. The slice was stained with anti-AGE antibody and examined through a microscope. The observation results are shown in Table 7.

TABLE 6

| NaCl | 97 mM/l |
|---|---|
| Na$_2$OOC•CH(OH)CH$_3$ | 17.5 mM/l |
| MgCl$_2$ | 0.75 mM/l |
| CaCl$_2$ | 1.75 mM/l |

Aqueous solution/methanol ratio: 9/1

Control 6

The solution (B) prepared by the addition of methylglyoxal into the mixed solution (A) in Control 5, was infused in the same manner as Control 5. The rat peritoneum tissue was stained with anti-AGE antibody and examined in the same way. The observation results are shown in Table 7.

Example 13

The solution (c) that is prepared by addition of electrolytes in Table 6, methylglyoxal (20 mM/l) and N-phenacyl thiazolium bromide (20 mM/l) into the mixed solution of water and methanol (1/9), in place of the solution (B) in Control 6, was infused in the same manner as Control 6. The rat peritoneum tissue was stained with anti-AGE antibody and examined in the same way. The observation result is shown in Table 7.

Example 14

The infusion was performed in the same manner as those in Control 6 for 5 days, thence the rat peritoneal cavity was rinsed, For another 5 days the rat was intraperitoneally infused 15 ml of the solution (D), which was prepared by removing methylglyoxal from the solution (C), every day. The peritoneum tissue slice was submitted to anti-AGE antibody staining test. The result is shown in Table 7.

TABLE 7

|  | Solution | Additives | Anti-AGE antibody staining test |
|---|---|---|---|
| Control 5 | (A) | None | ○ |
| Control 6 | (B) | Methylglyoxal | X |
| Example 13 | (C)* | Methylglyoxal + N-Phenacyl Thiazolium bromide | ○ |
| Example 14 | (D)* | After 5 ay infusion of the solution(B), N-Phenacyl thiazolium bromide alone infused for another 5 days | ○ |

○: Not stained with anti-AGE antibody
X: Stained with anti-AGE antibody
*Solution; electrolytes in the mixture of water/methanol: 9/1

It is apparent in Table 7, that the solution (A), which does not contain GDPs, did not form AGE in peritoneum, while in the case of the solution (B) which contains GDP, the formation of AGE was clearly observed in the peritoneum tissue. In contrast, the solution (C), which was added N-phenacylthiazolium bromide, did not form AGE.

While, in the case of the second 5 days infusion with the solution (D) which contains N-phenacyl thiazolium bromide, the AGE, formed on the peritoneum tissue through the first 5 days infusion, disappeared. It indicates that protein cross linkage may be split by N-phenacyl thiazolium bromide.

INDUSTRIAL APPLICABILITY

Peritoneal dialysis is favorable therapy for end stage renal disease as it is physiological dialysis and it allows the patients enjoy social activities. However, the removal of excess liquid is proceeded by hyper-osmolarity of the dialysate, so that the osmotic agent, glucose and its degradation products cause cross linking of the protein that consists of peritoneum, resulting in encapsulated peritoneum sclerosis, which prevents continuation of this therapy.

The present invention can supply the dialysate to solve this problem, that is, protecting the peritoneum by adding protein cross linking suppressors into the dialysate, or healing the peritoneum, which is suffering from sclerosis to some extent, by adding protein cross linkage splitters into the dialysate to allow the patients keep on the therapy for long period without suffering from peritoneum sclerosis, and to retain ultra filtration capacity. So that the present invention supplies an effective means to enable the therapy keeping on without problem.

The invention claimed is:

1. A preparation method of a dialysate for peritoneal dialysis which comprises sterilizing dialysate under high temperature and pressure, and thereafter mixing the dialysate with an amount of filter sterilized sodium thiosulfate effective to quench glucose degradation products and suppress protein crosslinking of peritoneum.

* * * * *